US007938800B2

(12) United States Patent
Koh

(10) Patent No.: US 7,938,800 B2
(45) Date of Patent: May 10, 2011

(54) NEEDLESHIELD ASSEMBLY AND METHODS OF USE

(75) Inventor: Lawrence R. Koh, Sherman Oaks, CA (US)

(73) Assignee: Lawrence R. Koh and Nina Merrell-Koh, Sherman Oaks, CA (US), Trustees, or their Successors & assigns, under the Lawrence R. Koh and Nina Merrell-Koh family Trust dated December 5, 1995

( * ) Notice: Subject to any disclaimer, the term of this patent is extended or adjusted under 35 U.S.C. 154(b) by 183 days.

(21) Appl. No.: 12/350,825

(22) Filed: Jan. 8, 2009

(65) Prior Publication Data
US 2009/0287149 A1 Nov. 19, 2009

Related U.S. Application Data

(60) Provisional application No. 61/052,927, filed on May 13, 2008.

(51) Int. Cl.
*A61M 5/00* (2006.01)
*A61M 5/32* (2006.01)
(52) U.S. Cl. ........................................ 604/110; 604/198
(58) Field of Classification Search .................... 604/110
See application file for complete search history.

(56) References Cited

U.S. PATENT DOCUMENTS

| | | | |
|---|---|---|---|
| 2,512,568 A | 6/1950 | Saffir | |
| 2,512,569 A | 6/1950 | Saffir | |
| 2,954,768 A | 10/1960 | Hamilton | |
| 3,890,970 A | 6/1975 | Gullen | |
| 4,838,877 A | 6/1989 | Massau | |
| 4,867,172 A | 9/1989 | Haber et al. | |
| 4,935,013 A * | 6/1990 | Haber et al. | 604/192 |
| 4,950,250 A | 8/1990 | Haber et al. | |
| 5,120,309 A | 6/1992 | Watts | |
| 5,151,231 A | 9/1992 | Lambert et al. | |
| 5,250,066 A | 10/1993 | Lambert | |
| 5,312,376 A | 5/1994 | Van Heugten | |
| 5,456,875 A | 10/1995 | Lambert | |
| 5,458,614 A | 10/1995 | Humphrey | |
| 5,569,213 A | 10/1996 | Humphrey | |
| 5,607,401 A | 3/1997 | Humphrey | |
| 5,620,639 A | 4/1997 | Stevens | |
| 5,632,728 A | 5/1997 | Hein | |
| 5,637,399 A | 6/1997 | Yoshikawa et al. | |
| 5,669,890 A | 9/1997 | Grimm | |
| 5,738,665 A * | 4/1998 | Caizza et al. | 604/263 |
| 5,814,018 A | 9/1998 | Elson et al. | |
| 5,823,997 A | 10/1998 | Thorne | |
| 5,910,130 A | 6/1999 | Caizza et al. | |

(Continued)

FOREIGN PATENT DOCUMENTS
EP 0 713 710 A1 5/1995
(Continued)

*Primary Examiner* — Nicholas D Lucchesi
*Assistant Examiner* — Jason Flick
(74) *Attorney, Agent, or Firm* — Loza & Loza, LLP; Heidi L. Eisenhut

(57) ABSTRACT

A needleshield assembly including an extensible frame, an actuator, a needle and a dispensing device attachment member is disclosed. The extensible frame is capable of moving from a collapsed position to an extended position upon pressure applied to the actuator. In the extended position, the extensible frame both protects the distal end of a needle and renders the needle immobile.

18 Claims, 10 Drawing Sheets

U.S. PATENT DOCUMENTS

| | | | |
|---|---|---|---|
| 5,925,020 A * | 7/1999 | Nestell | 604/198 |
| 5,980,488 A | 11/1999 | Thorne | |
| 6,015,397 A * | 1/2000 | Elson et al. | 604/192 |
| 6,096,012 A | 8/2000 | Bogert et al. | |
| 6,224,576 B1 | 5/2001 | Thorne, Jr. et al. | |
| 6,254,575 B1 | 7/2001 | Thorne, Jr. et al. | |
| 6,280,420 B1 | 8/2001 | Ferguson et al. | |
| 6,500,157 B2 | 12/2002 | Luther | |
| 6,527,747 B2 | 3/2003 | Adams et al. | |
| 6,767,496 B1 | 7/2004 | Jensen et al. | |
| 6,796,968 B2 | 9/2004 | Ferguson et al. | |
| 6,863,662 B2 | 3/2005 | Luther | |
| 6,949,086 B2 | 9/2005 | Ferguson et al. | |
| 6,986,759 B1 | 1/2006 | Jeremijevic | |
| 6,997,902 B2 | 2/2006 | Thorne et al. | |
| 7,001,363 B2 | 2/2006 | Ferguson et al. | |
| 7,029,461 B2 | 4/2006 | Ferguson et al. | |
| 7,147,623 B2 | 12/2006 | Mathiasen | |
| 7,198,618 B2 | 4/2007 | Ferguson et al. | |
| 7,316,668 B2 | 1/2008 | Swenson | |
| 7,320,682 B2 | 1/2008 | Cocker et al. | |
| 2002/0062107 A1 | 5/2002 | Parmigiani et al. | |
| 2003/0028154 A1 | 2/2003 | Ross | |
| 2003/0229317 A1 * | 12/2003 | Ferguson et al. | 604/263 |
| 2004/0193120 A1 | 9/2004 | Ferguson et al. | |
| 2004/0199127 A1 | 10/2004 | Jensen et al. | |
| 2005/0283125 A1 | 12/2005 | Barkhahn et al. | |
| 2006/0111670 A1 | 5/2006 | Yerman | |
| 2006/0129106 A1 | 6/2006 | Ferguson et al. | |
| 2007/0073249 A1 | 3/2007 | Zambaux et al. | |
| 2007/0083159 A1 | 4/2007 | Woehr et al. | |
| 2007/0100296 A1 | 5/2007 | Hwang | |
| 2007/0179455 A1 | 8/2007 | Geliebter et al. | |
| 2008/0051724 A1 | 2/2008 | Bedford et al. | |

FOREIGN PATENT DOCUMENTS

| | | |
|---|---|---|
| WO | WO 98/13081 | 4/1998 |

* cited by examiner

NEEDLESHIELD ASSEMBLY AND METHODS OF USE

CLAIM OF PRIORITY UNDER 35 U.S.C. §119

The present Utility Application for Patent claims priority to U.S. Provisional Application No. 61/052,927 entitled "Needleshield Assembly & Methods of Use" filed May 13, 2008, and hereby expressly incorporated by reference herein.

FIELD

The present application relates to hypodermic needles, and more particularly, to disposable, non-reusable needles with shields.

BACKGROUND

Hypodermic syringes are used with hypodermic needles to inject liquid or gases into body tissues or to remove blood or other fluid or fluid-like samples from the body. The barrel of a syringe can be made of plastic or glass and usually has graduated marks indicating the volume of fluid in the syringe. The barrel of a syringe is nearly always transparent. Most modern medical syringes are plastic with a rubber piston because this type of syringe seals much better between the piston and the barrel and because they are cheap enough to dispose of after being used only once. Very serious problems can arise with needle re-use especially in use outside of health care settings and use in third world countries.

At least 3 billion injections occur yearly outside of health care settings. About 2 billion of these injections are administered by people with diabetes and patients receiving home health care. Approximately 1 billion are attributed to injection drug users (IDUs) using illicit drugs like heroin and cocaine. Most of the needles used for these injections end up discarded in household trash and community solid waste, putting workers and the public at risk of needle stick injuries and potentially fatal infections. A surprise encounter with a used syringe or needle in a playground, park, or at work can provoke intense fears of injury and life-threatening infections. If a needle stick injury occurs, the costs of providing post-injury counseling and prevention measures are significant. Problems that can arise from unsafely discarded used syringes and needles include needle stick injuries and potentially fatal blood borne infections, such as human immune deficiency virus (HIV) and hepatitis B and C.

Even in a controlled setting such as a hospital or other healthcare facility, an accidental needle stick injury is a constant occupational hazard for healthcare workers and other employees working in such a setting. Although such facilities generally provide disposal containers (e.g., Covidien™ Sharps Containers), improper disposal of syringes and needles can increase the risk of an accidental needle stick injury. For example, a healthcare worker or employee may not be properly educated in the proper disposal of needles or may inadvertently dispose of a used needle in the regular trash. Also, a healthcare worker may sustain an accidental needle stick when administering medication to a patient. In one scenario, a healthcare worker may sustain an accidental needle stick when administering medication to an epileptic patient.

Consequently, a needleshield assembly is needed for rendering a dispensing device, such as a syringe, non-usable after a single use.

SUMMARY

A needleshield assembly, including: (a) a dispensing device attachment member adapted to attach the needleshield assembly to a needle hub of a dispensing device; (b) an extensible frame including a distal member and a proximal member, the extensible frame connected to a proximal end of the dispensing device attachment member by a first hinge, the distal member and the proximal member connected by a second hinge at a distal end of the proximal member and a proximal end of the distal member, the extensible frame having a collapsed position and an extended position; and (c) an actuator attached to the proximal end of the dispensing device attachment member by a third hinge, the actuator adapted to direct the extensible frame from the collapsed position to the extended position is herein disclosed.

The distal member may further include: (a) a proximal sub-portion and a distal sub-portion; (b) at least one aperture adapted to receive a distal end of the needle, the at least one aperture connecting the proximal sub-portion to the distal sub-portion of the distal member; (c) at least one set of hooks adapted to immovably secure the needle when the extensible frame is in the extended position; and (d) an enclosing member adapted to enclose the distal end of the needle when in the extended position, the enclosing member comprising the distal end of the distal sub-portion.

A first set of hooks is positioned on a top face of the distal sub-portion and a second set of hooks is positioned on a bottom face of the proximal sub-portion. In one embodiment, each set of hooks include two opposing members. The needleshield assembly may further include: (a) a hooking mechanism including a set of clips on a proximal end of the dispensing device attachment member and a set of corresponding latching mechanisms on a proximal end of the extensible member; and (b) a needle positioned within a bore of the dispensing device attachment member, the needle in fluid communication with a fluid chamber of the dispensing device forming a fluid path when attached to the dispensing device with the extensible frame in the collapsed position.

The actuator further may include: (a) a blocking protrusion adapted to puncture a wall of the dispensing device attachment member and block the fluid path when the extensible frame is in the extended position; and (b) a retaining member adapted to secure the blocking protrusion in the fluid path. The needleshield assembly further includes a pressure pad on the proximal member of the extensible frame and capable of contact with the actuator. In one embodiment, a portion of the wall of the dispensing device attachment member functions to block the fluid path when the extensible frame is moved from the collapsed position to the extended position. The needleshield assembly may further include a removable cap to enclose the needle when the extensible frame is in the collapsed position. The needleshield assembly may further include a plurality of ribs about the periphery of the dispensing device attachment member for securing the removable cap.

A method of rendering a dispensing device non-usable after a single use thereof, including: (a) coupling a needleshield assembly to the dispensing device, wherein the needleshield assembly includes: (i) a dispensing device attachment member adapted to attach the needleshield assembly to a needle hub of a dispensing device; (ii) an extensible frame including a distal member and a proximal member, the extensible frame connected to a proximal end of the dispensing device attachment member by a first hinge, the distal member and the proximal member connected by a second hinge at a distal end of the proximal member and a proximal end of the distal member, the extensible frame having a collapsed position and an extended position; (iii) an actuator attached to the proximal end of the dispensing device attachment member by a third hinge, the actuator adapted to direct the extensible frame from the collapsed position to the extended position; and (iv) a needle positioned within a bore of the dispensing device attachment member, the needle in fluid communication with a fluid chamber of the dispensing device forming a fluid path when attached to the dispensing device with the extensible frame in the collapsed position; (b) removing a cap covering the needle; (c) drawing a fluid through the needle thereby filling the fluid chamber of the dispensing device; and (d) applying pressure to the actuator to direct the extensible frame from the collapsed position to the extended position thereby rendering the dispensing device non-reusable is herein disclosed.

Applying pressure to the actuator may cause a blocking protrusion on the actuator to puncture a wall of the dispensing device attachment member and block the fluid path. Furthermore, applying pressure to the actuator further may cause a retaining member on the actuator to secure the blocking protrusion in the fluid path. Furthermore, applying pressure to the actuator may cause an aperture on the distal member encircling the needle to guide the needleshield assembly from the collapsed position to the extended position. Furthermore, applying pressure to the actuator may cause at least one set of hooks on the distal member to immovably secure the needle when the extensible frame is in the extended position. Furthermore, applying pressure to the actuator may cause an enclosing member on the distal member to enclose a distal end of the needle when the extensible frame is in the extended position. Furthermore, applying pressure to the actuator may cause a portion of the wall of the dispensing device functions to block the fluid path when the extensible frame is in the extended position.

A method of preventing a dispensing device from being re-used after single use thereof, including: (a) blocking a fluid path between a fluid chamber of the dispensing device and a fluid bore of a needle, wherein the fluid chamber and the fluid bore form the fluid path when the dispensing device and the needle are coupled together; and (b) immobilizing the needle by a plurality of hooks, wherein the dispensing device has a needleshield assembly attached thereto, the needleshield assembly including: (i) a dispensing device attachment member attached to a needle hub of the dispensing device, (ii) an extensible frame including a distal member and a proximal member, the extensible frame connected to a proximal end of the dispensing device attachment member by a first hinge, the distal member and the proximal member connected by a second hinge at a distal end of the proximal member and a proximal end of the distal member, the extensible frame having a collapsed position and an extended position, (iii) an actuator attached to the proximal end of the dispensing device attachment member by a third hinge, the actuator having a blocking protrusion and a retaining member, and (iv) the needle positioned within a bore of the dispensing device attachment member is herein disclosed.

Blocking the fluid path may include causing a portion of a wall of the dispensing device attachment member and the blocking protrusion of the actuator to block the fluid path. The plurality of the hooks may secure a periphery of the needle in at least two positions.

BRIEF DESCRIPTION OF DRAWINGS

The features, nature, and advantages of the present aspects may become more apparent from the detailed description set forth below when taken in conjunction with the drawings in which like reference characters identify correspondingly throughout.

DETAILED DESCRIPTION

The following detailed description is of the best currently contemplated modes of carrying out the present application. The description is not to be taken in a limiting sense, but is made merely for the purpose of illustrating the general principles of the present application.

Figure 1:
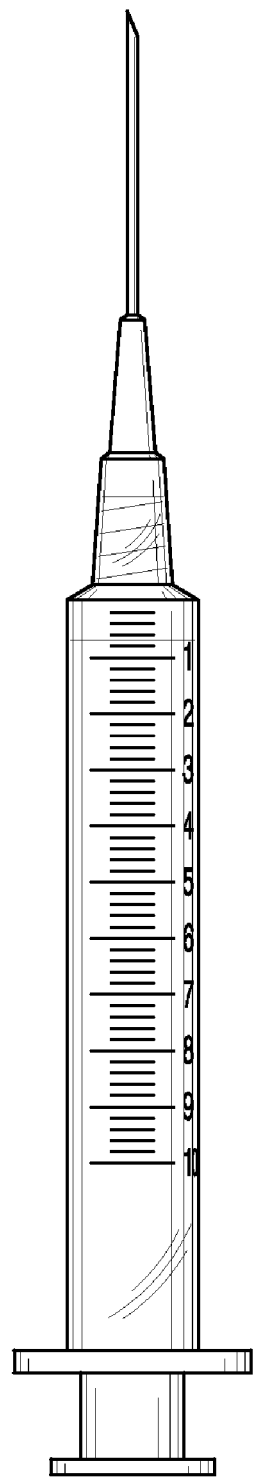
FIG. 1 illustrates a prior art syringe and hypodermic needle with attached Luer Lock.
Figure 2:
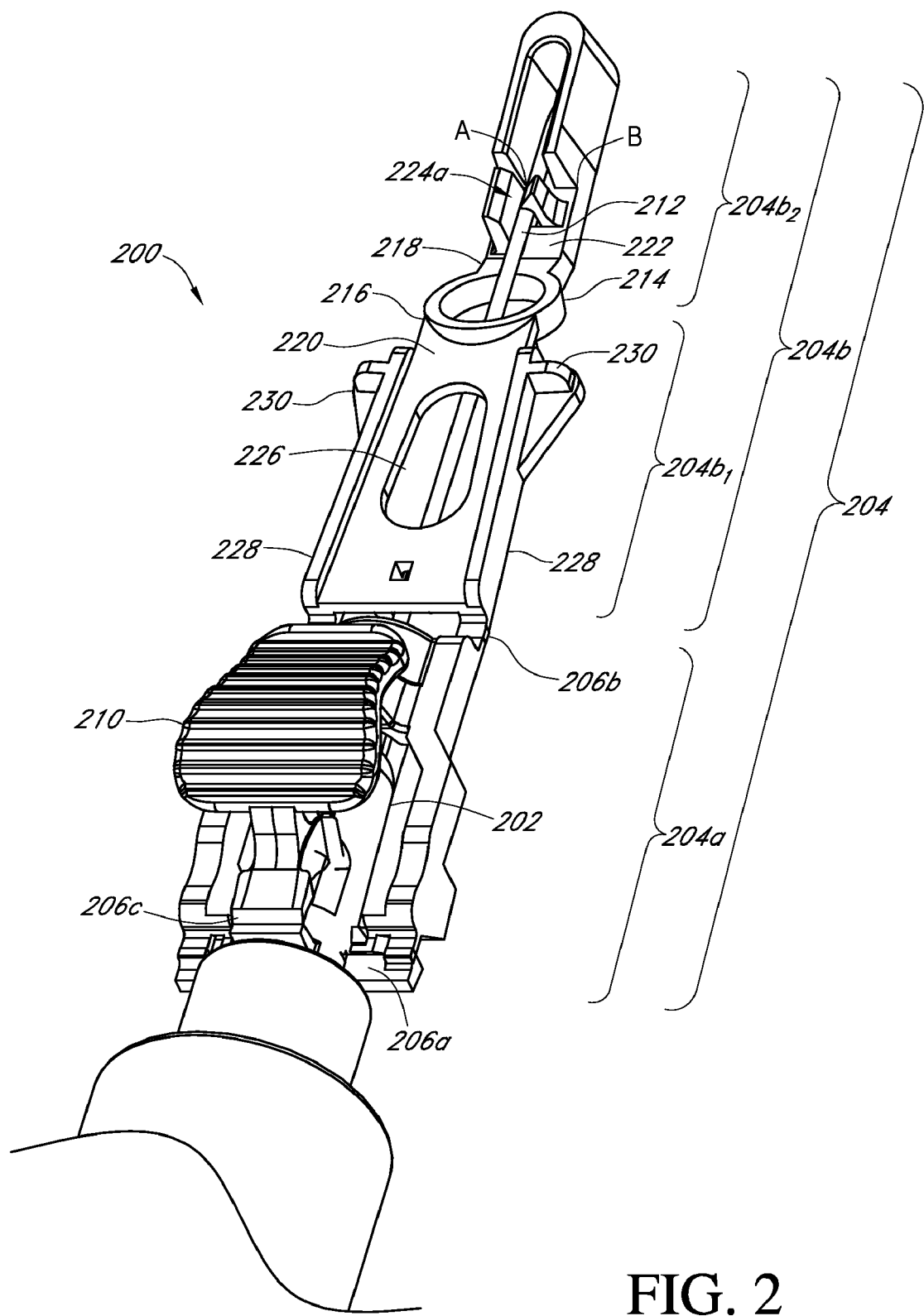
FIG. 2 illustrates a top perspective view of an embodiment of a needleshield assembly in an extended position.

Embodiments of needleshield assemblies and methods of use are provided herein. FIG. 1 illustrates a prior art syringe and hypodermic needle with attached Luer Lock. FIG. 2 illustrates a top perspective view of a needleshield assembly 200 in an extended position according to an embodiment of the invention. According to this embodiment, the needleshield assembly 200 includes a dispensing device attachment member 202 (partially shown, see FIG. 3) connected to an extensible frame 204 by a first flexible hinge 206a. In one embodiment, edges of the extensible frame 204 angle inward toward each other from a proximal end to a distal end of the extensible frame 204. The extensible frame 204 may include proximal member 204a and distal member 204b connected by a second flexible hinge 206b. An actuator 210 may be connected to the dispensing device attachment member 202 by a third flexible hinge 206c. The actuator 210 may be approximately concave in shape; however, other suitable shapes are within the scope of the invention. In one embodiment, the actuator 210 may be capable of directing the extensible frame 204 from a collapsed position (see FIGS. 3-4) to an extended position (as shown) when pressure is applied thereto. In some embodiments, the actuator 210 may include friction grooves on the surface to prevent slipping of an operator's thumb when in use. The needleshield assembly 200 may also include a needle 212 positioned within a bore (not shown, see FIG. 4) of the dispensing device attachment member 202.

The distal member 204b of the extensible frame 204 may include two sub-portions, namely, proximal sub-portion $204b_1$ and distal sub-portion $204b_2$, connected via a rimmed aperture 214 therebetween. A distal end 216 of sub-portion $204b_1$ may terminate approximately concavely while a proximal end 218 of sub-portion $204b_2$ may initiate approximately polygonally. According to one embodiment, the distal end 216 of sub-portion $204b_1$ and the proximal end 218 of sub-portion $204b_2$ may be situated at approximately 180° relative to one another on the aperture 214. Distal end 216 of sub-portion $204b_1$ and proximal end 218 of sub-portion $204b_2$ may provide the connection between sub-portions $204b_1$ and $204b_2$ and may be integral parts of distal member $204b$. In an alternative embodiment, distal end 216 of sub-portion $204b_1$ and proximal end 218 of sub-portion $204b_2$ may be flexible hinges. Aperture 214 may be angled such that a top surface 220 of sub-portion $204b_1$ is in a different plane relative to a top surface 222 of sub-portion $204b_2$. The angle may from about 0.5° to about 45°. This configuration allows the needleshield assembly 200 to partially, substantially or completely protect a distal end of the needle 212 when in the extended position as shown in FIG. 2. More particularly, as shown in FIG. 2, when in the extended position, the distal end of the needle 212 may pass through the rimmed aperture 214 and terminate within sub-portion $204b_2$ (explained in more detail below). During movement from the collapsed position to the extended position, the rimmed aperture 214 may serve as a guide for sub-portion $204b_2$ as sub-portion $204b_2$ is being positioned onto the distal end of the needle 212.

Sub-portion $204b_2$ may include a closed bottom face, an open top face and a partial sidewall, i.e., "enclosed member". In some embodiments, sub-portion $204b_2$ approximates a parabola in shape; however, it should be appreciated that the edges of sub-portion $204b_2$ are approximately equidistant relative to the axis of symmetry until it approaches the vertex. The partial sidewall may initiate at a point A on sub-portion $204b_2$, continue over the vertex, and terminate at a point B on sub-portion $204b_2$ equal and opposite to point A. When the needleshield assembly 200 is moved from a collapsed position to an extended position, the open top face may receive the distal end of the needle 212. Thus, when in the extended position, sub-portion $204b_2$ of the extensible frame 204 may partially, substantially or completely enclose the distal end of the needle 212 thereby preventing an accidental needle stick after use. More particularly, the partial sidewall of sub-portion $204b_2$ retains the distal end of the needle 212 within the open face of sub-portion $204b_2$. Also shown are a first set of hooks 224a situated on the top surface 222 of the open face of sub-portion $204b_2$ (explained in more detail below).

Sub-portion $204b_1$ may include a top face and a bottom face with an opening 226 substantially centered therein. The opening 226 may provide visual guidance when an operator activates the needleshield assembly from the collapsed position to the extended position. Additionally, the opening 226 may function as a "catch" for a thumb of the operator when the operator activates the needleshield assembly 200 from the collapsed position to the extended position thereby assisting in preventing the thumb from approaching the distal end of the needle 212 when pressure is applied to the actuator 210. Flanges 228 flank edges of sub-portion $204b_1$ and may terminate in winged protrusions 230. Similar to the opening 226, the flanges 228 may assist in preventing the thumb of the operator from approaching the distal end of the needle 212 when pressure is applied to the actuator 210 in addition to providing other functions (explained in more detail below).

Figure 3A:
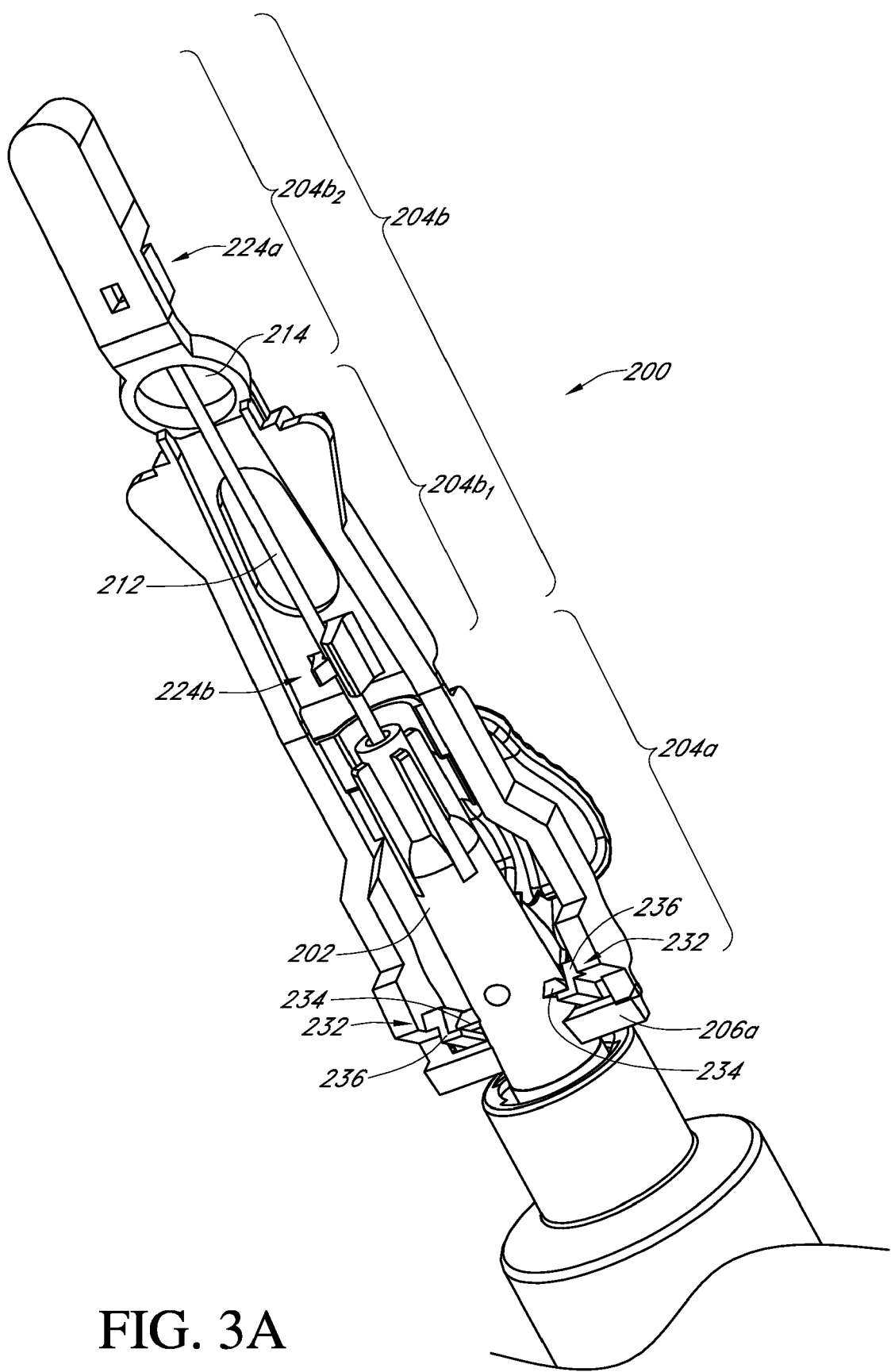
FIG. 3A illustrates a bottom perspective view of an embodiment of a needleshield assembly in an extended position.

FIG. 3A illustrates a bottom perspective view of the needleshield assembly 200 of FIG. 2. In one embodiment, a bottom face of the proximal member 204a may be substantially open as is a bottom face of sub-portion $204b_1$ (up until aperture 214) of distal member 204b. This configuration may allow for the extensible frame 204 to partially, substantially or completely shield the shaft of the needle 212 once the needleshield assembly 200 is moved from the collapsed position to the extended position. Moreover, as shown, a bottom face and partial sidewall of sub-portion $204b_2$ may be substantially closed. As explained previously, this configuration enables partial, substantial or complete enclosure of the distal end of the needle 212 thereby preventing an accidental needle stick after use.

Distal member 204b may include at least one set of hooks (also see FIG. 2) capable of immovably securing the needle 212 when the needleshield assembly 200 is in the extended position. The set of hooks may include two opposing members (also see FIG. 2). In one embodiment, one opposing member is larger than the other opposing member. The larger opposing member may include a ribbed top surface, while the smaller opposing member may include a hook-like flange. Thus, when the needle 212 passes through the two opposing members, the hook-like flange of the smaller opposing member hooks onto the ribbed top surface of the larger opposing member thereby securing the shaft of the needle. In one embodiment, sub-portion $204b_2$ includes a first set of hooks 224a (see FIG. 2) and sub-portion $204b_1$ includes a second set of hooks 224b. According to this configuration, the needle 212 can be immovably secured when the needleshield assembly 200 is in the extended position after use thereof. As a result, hooks 224a and 224b may prevent the needleshield assembly 200 from being altered from the extended position back into the collapsed position, thereby preventing re-use. Also, by securely grasping the shaft of the needle 212, hooks 224a and 224b may operate to prevent the needleshield assembly 200 from collapsing in the event of a head-on impact.

Figure 3B:
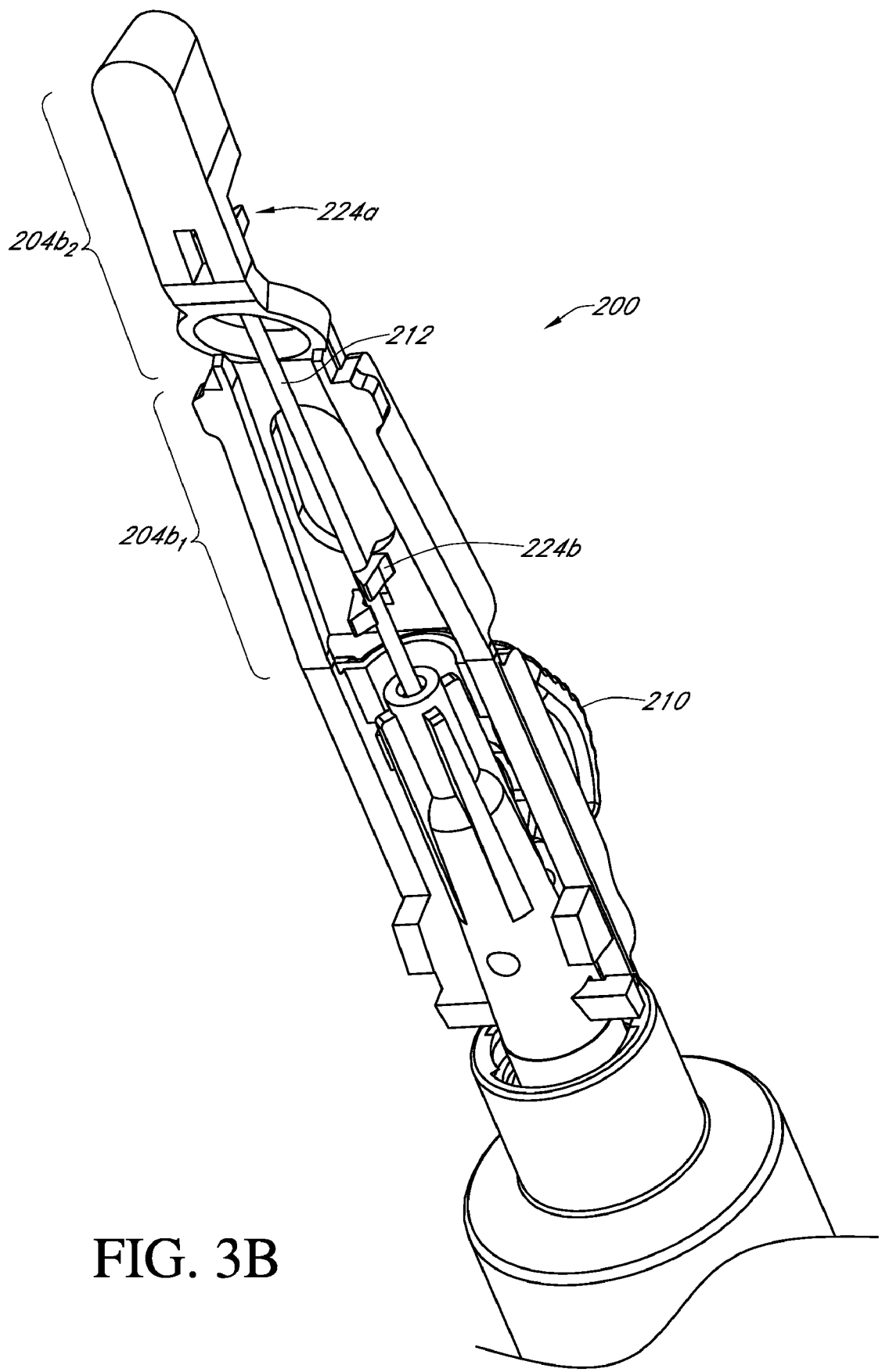
FIG. 3B illustrates a bottom perspective view of an alternative embodiment of a needleshield assembly in an extended position.

In an alternative embodiment, as shown in FIG. 3B, the set of hooks may include two opposing members staggered relative to one another and at a distance from one another. In one embodiment, sub-portion $204b_1$ may include a set of hooks 224b and sub-portion $204b_2$ may include another set of hooks 224a in a staggered configuration. This configuration may allow the needle 212 to be immovably secured when the needleshield assembly 200 is in the extended position after use thereof. As a result, each set of hooks, e.g., the set of hooks 224b, may prevent the needleshield assembly 200 from being altered from the extended position back into the collapsed position, thereby preventing re-use. Also, by securely grasping the shaft of the needle 212, each set of hooks 224a and 224b (in additional to other components described previously) may operate to prevent the needleshield assembly 200 from collapsing in the event of a head-on impact. Although some components of the needleshield assembly 200 appear different as shown in FIG. 3B relative to similar components of the needleshield assembly 200 as shown in FIG. 3A, it should be appreciated that any of these other components may be interchangeable without changing the overall features and benefits of embodiments of the invention.

Continuing to refer to FIG. 3A, Proximal member 204a may include at least one additional hooking mechanism 232 on a bottom surface thereof and near the first flexible hinge 206a. The hooking mechanism 232 may include a clip 234 integral with the dispensing device attachment member 202 and a latching mechanism 236 integral on a bottom surface of the proximal member 204a. When the needleshield assembly 200 is moved from the collapsed position to the extended position, the latching mechanism 236 engages the clip 234 thereby preventing the extensible frame 204 from breaking away from the dispensing device attachment member 202. Although the clip 234 initially resists engagement with the latching mechanism 236, once it does, it will not disengage easily thereby providing an additional safety measure. In one embodiment, at least two (2) clips 234 are positioned approximately 180° from one another about the base of the dispensing device attachment member 202 with at least two (2)

corresponding latching mechanisms 236 positioned at the base of the extensible member 204.

Figure 4:
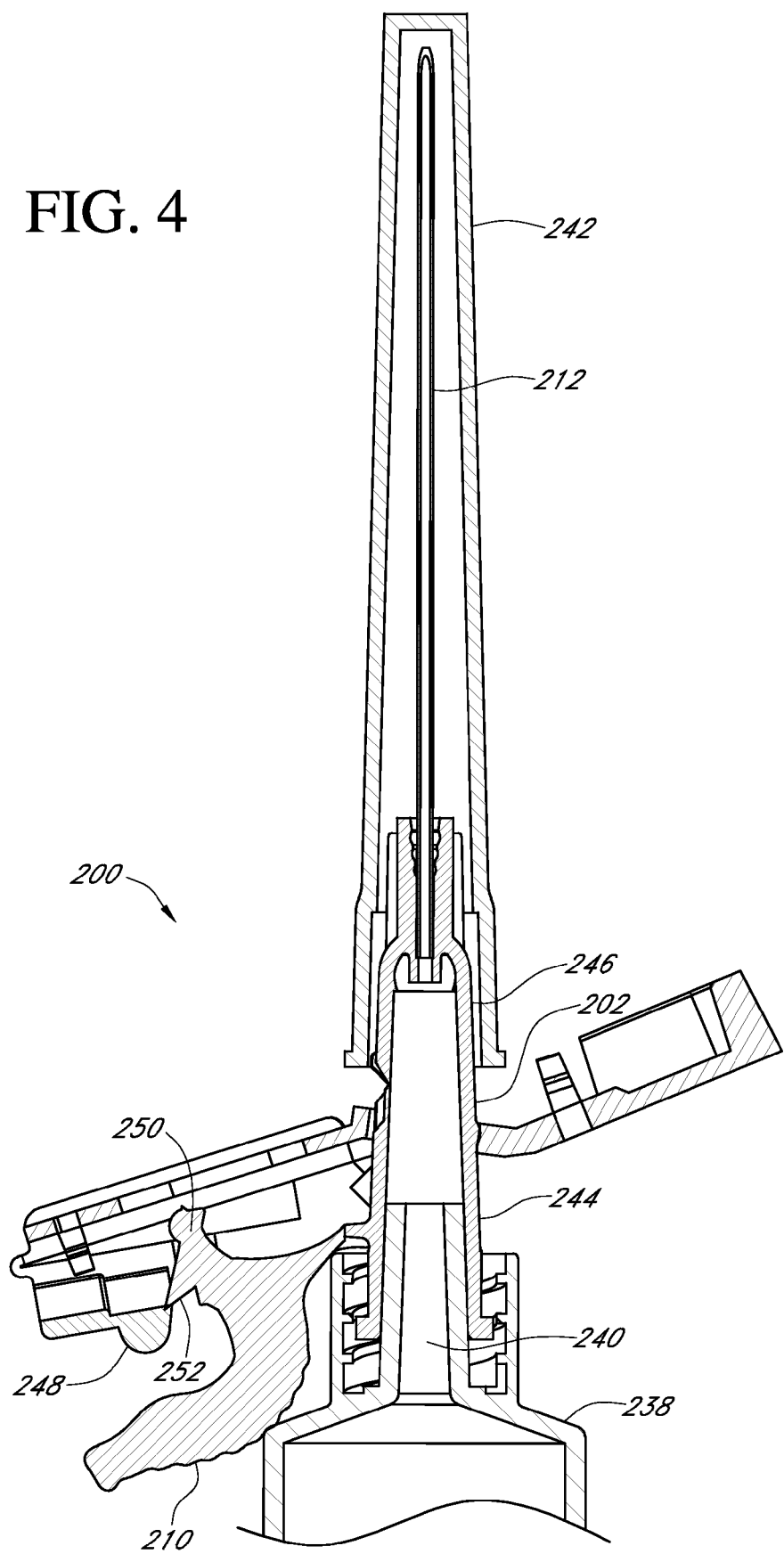
FIG. 4 illustrates a cross-sectional side view of an embodiment of a needleshield assembly in a collapsed position.

FIG. 4 illustrates a cross-sectional side view of the needleshield assembly 200 of FIG. 2 in a collapsed position according to an embodiment of the present application. As shown, the needleshield assembly 200 is secured to a delivery device 238 by way of the dispensing device attachment member 202. The dispensing device attachment member 202 may couple to a fluid chamber 240 of delivery device 238 by, for example, a Luer Taper connection such as a Luer Lock or Luer Slip; however, other attachment mechanisms are suitable. In the embodiment illustrated in FIG. 4, the dispensing device attachment member 202 attaches to the fluid chamber 240 of delivery device 238 by a threaded Luer Taper. The delivery device 238 may be, for example, a syringe, a catheter assembly, a blood transfusion connection or a peripheral. In the embodiment illustrated in FIG. 4, the dispensing device 238 is a syringe (only proximal end of the syringe is shown). A removable cap 242 may be secured to the needleshield assembly 200 by contact with a plurality of ribs (not shown, see FIG. 5) molded onto the assembly 200.

When the needleshield assembly 200 is in a collapsed position and secured to a delivery device, the needle 212 may be in fluid communication with the fluid chamber 240 of the delivery device 238 (partially shown). Before removal of the cap 242, the needleshield assembly 200 may stay in the collapsed position by way of the rimmed aperture 214 (not shown, see FIG. 3) which remains positioned between a first set of ribs 244 and a second set of ribs 246 (see FIG. 5). Upon removal of the cap 242, withdrawal and delivery of fluids may be performed by an operator with the needleshield assembly 200 in the collapsed position.

FIG. 4 also illustrates the actuator 210 in more detail. As shown, the actuator 210 may be positioned close to a pressure pad 248. When pressure is exerted on the actuator 210 by an operator, the pressure pad 248, in addition to the aperture 214, guide the extensible frame 204 from the collapsed position to the extended position. Also shown in FIG. 4 is the base of the actuator 210 which may include a blocking protrusion 250 in addition to a retaining member 252. The function of the blocking protrusion 250 and the retaining member 252 is explained in more detail below with reference to FIG. 6.

Figure 5A:
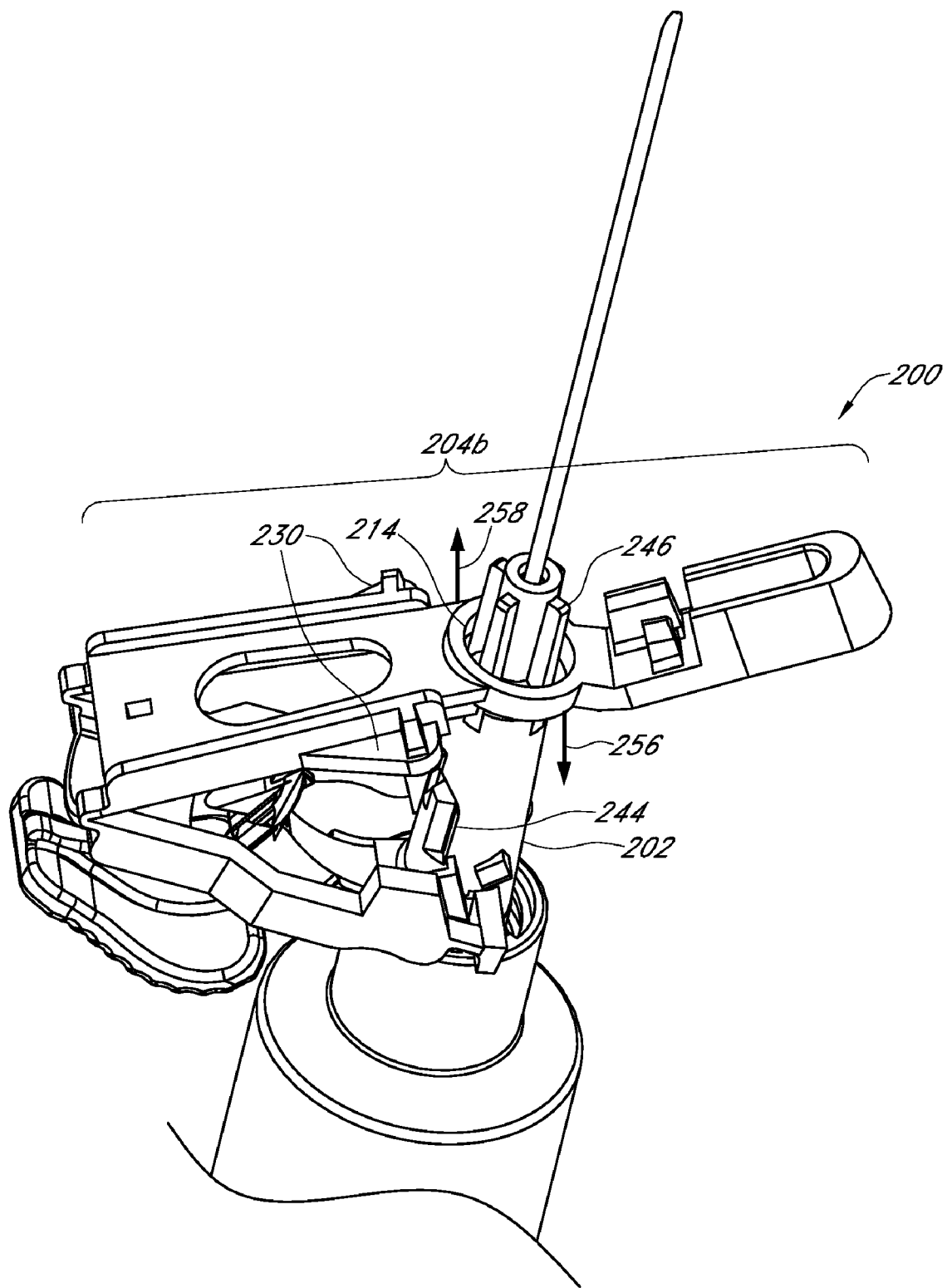
FIG. 5A illustrates a perspective view of an embodiment of a needleshield assembly in a collapsed position.

FIG. 5A illustrates a close-up perspective view of a needleshield assembly 200 in a collapsed position according to an embodiment of the present application. In this illustration, the first and second set of ribs 244 and 246 can be seen more clearly. The ribs 244 and 246 may be an integral part of the dispensing device attachment member 202. As explained briefly with reference to FIG. 4, the ribs 244 and 246 may function to retain the distal member 204$b$, via the rimmed aperture 214, when in the collapsed position. That is, during manufacturing, the rimmed aperture 214 may be forced between the ribs 244 and 246 to retain the distal member 204$b$ in the collapsed position in the direction indicated by arrow 256. On the other hand, during use by an operator, pressure applied to the actuator 210 may force the rimmed aperture 214 over the ribs 246 in the direction indicated by arrow 258. Additionally, ribs 244 may function to retain the cap 242 (not shown, see FIG. 4) as explained with reference to FIG. 4 above. Additionally, ribs 246 may function as a stopping mechanism for the winged protrusions 230 of sub-portion 204$b_1$. That is, during manufacturing, extensible frame 204 is prevented from partially, substantially or completely collapsing within itself when the winged protrusions 230 of sub-portion 204$b_1$ come into contact with ribs 246.

Figure 5B:
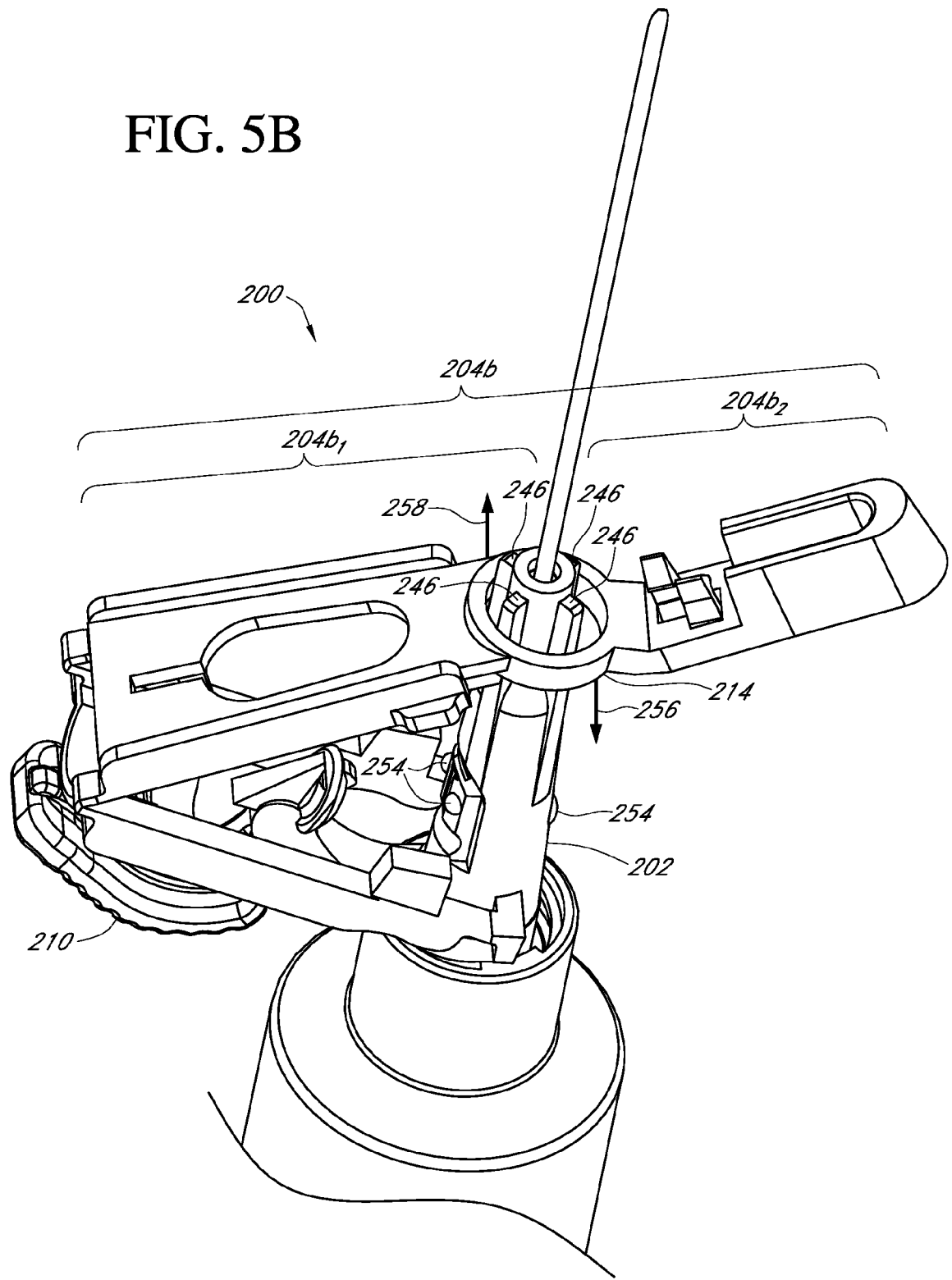
FIG. 5B illustrates a perspective view of an alternative embodiment of a needleshield assembly in a collapsed position.

In an alternative embodiment, as shown in FIG. 5B, a plurality of spherical protrusions 254 positioned about the base of the dispensing device attachment member 202 may function to retain the distal member 204$b$, via the rimmed aperture 214, when in the collapsed position. That is, during manufacturing, the rimmed aperture 214 may be forced over the spherical protrusions 254 in the direction indicated by arrow 256 to retain the distal member 204$b$ in the collapsed position. The spherical protrusions 254 may be sized such that the diameter of the circumference of a hypothetical circle encompassing the spherical protrusions 254 is slightly larger than the diameter of the rimmed aperture 214. In this manner, during use by an operator, pressure applied to the actuator 210 may force the rimmed aperture 214 over the spherical protrusions in the direction indicated by arrow 258. Although some components of the needleshield assembly 200 appear different as shown in FIG. 5B relative to similar components of the needleshield assembly 200 as shown in FIG. 5A, it should be appreciated that any of these other components may be interchangeable without changing the overall features and benefits of embodiments of the invention.

Figure 6:
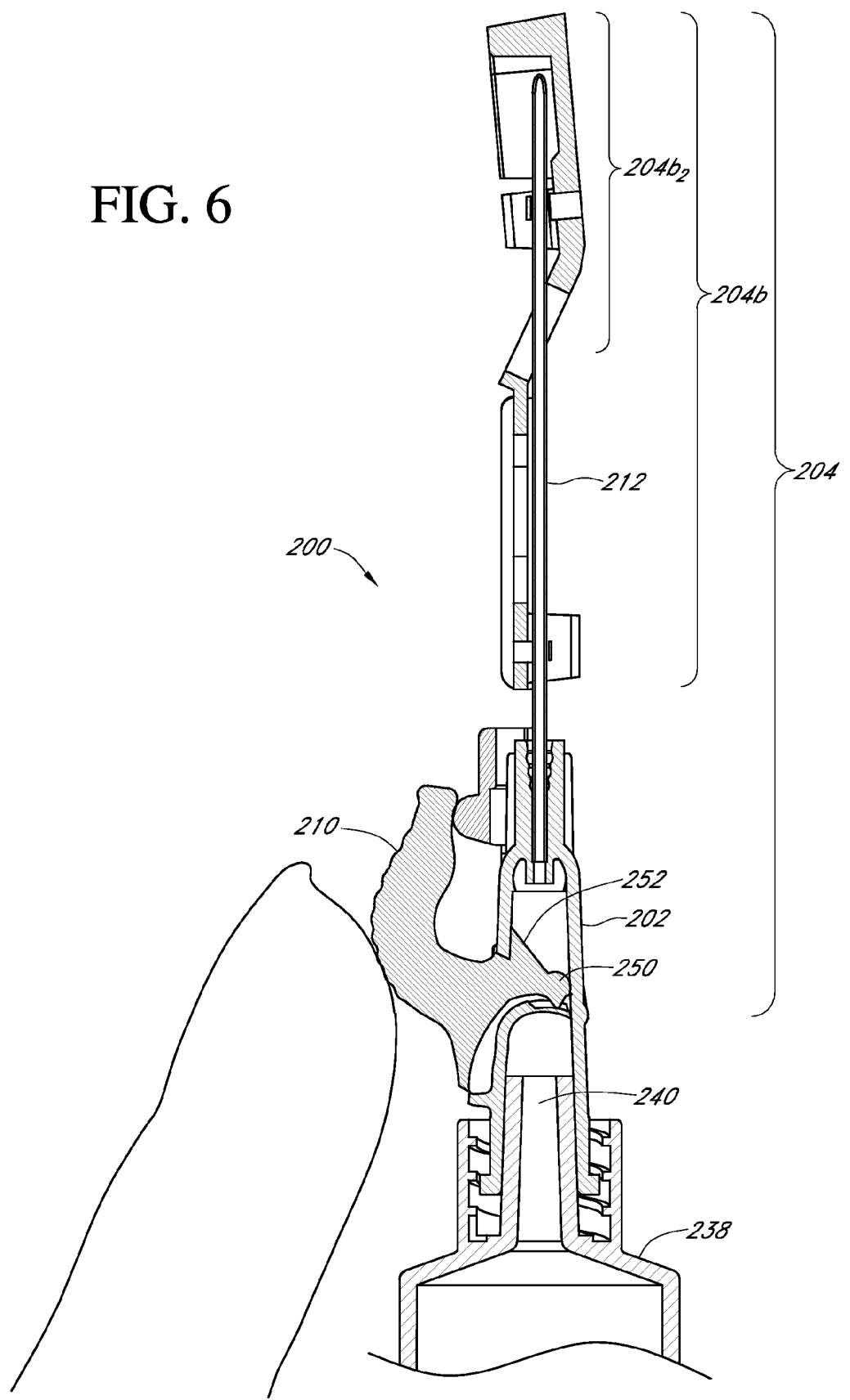
FIG. 6 illustrates a cross-sectional side view of an embodiment of a needleshield assembly in an extended position.

FIG. 6 illustrates a cross-sectional side view of the needleshield assembly 200 of FIGS. 2-3 in an extended position. The extended position may represent that the delivery device 238 has already been used and is ready for disposal. Upon pressure being exerted on the actuator 210, the extensible frame 204 may be fully extended about the shaft of the needle 212 and the tip of the needle 212 may be enclosed within sub-portion 204$b_2$ of distal member 204$b$ of extensible frame 204. As shown, upon movement from the collapsed position to the extended position, the blocking protrusion 250 of the actuator 210 may have punctured a portion of the wall of the dispensing device attachment member 202 thereby blocking the fluid path between the fluid chamber 240 and the needle 212 and preventing re-use. Moreover, the portion of the wall now lodged within the dispensing device attachment member 202 may also function to block the fluid path between the fluid chamber 240 and the needle 212. Simultaneously, the retaining member 252 may lodge against the wall of the dispensing device attachment member 202 to resist an operator's motion to reverse the extensible frame 204 from the extended position to the collapsed position thereby preventing re-use.

In one embodiment, a portion of a circumferential interior of the dispensing device attachment member 202 may be differently shaped at approximately the place in which the portion of the wall is lodged within dispensing device attachment member 202 relative to the remainder of the interior. For example, the circumferential interior of the dispensing device attachment member 202 may be approximately hour-glass shaped; however, other configurations are within the scope of the invention. More particularly, a ledge or ledges may be situated within the circumferential interior at this portion in order to obtain a better seal between the portion of the wall of the dispensing device attachment member 202 lodged inside of the dispensing device attachment member 202 (i.e., by the actuator 210 when pressure is applied thereto) and the interior of the dispensing device attachment member 202. In one embodiment, two (2) ledges may be situated within the circumferential interior of the dispensing device attachment member 202 which may better conform the interior of the dispensing device attachment member 202 to the shape of the portion of the wall lodged inside of the dispensing device attachment member 202 thereby producing a better seal to block medication traveling from the syringe and ensure the wall cannot be pried out of the dispensing device attachment member 202 once it is lodged therein.

Figure 7:
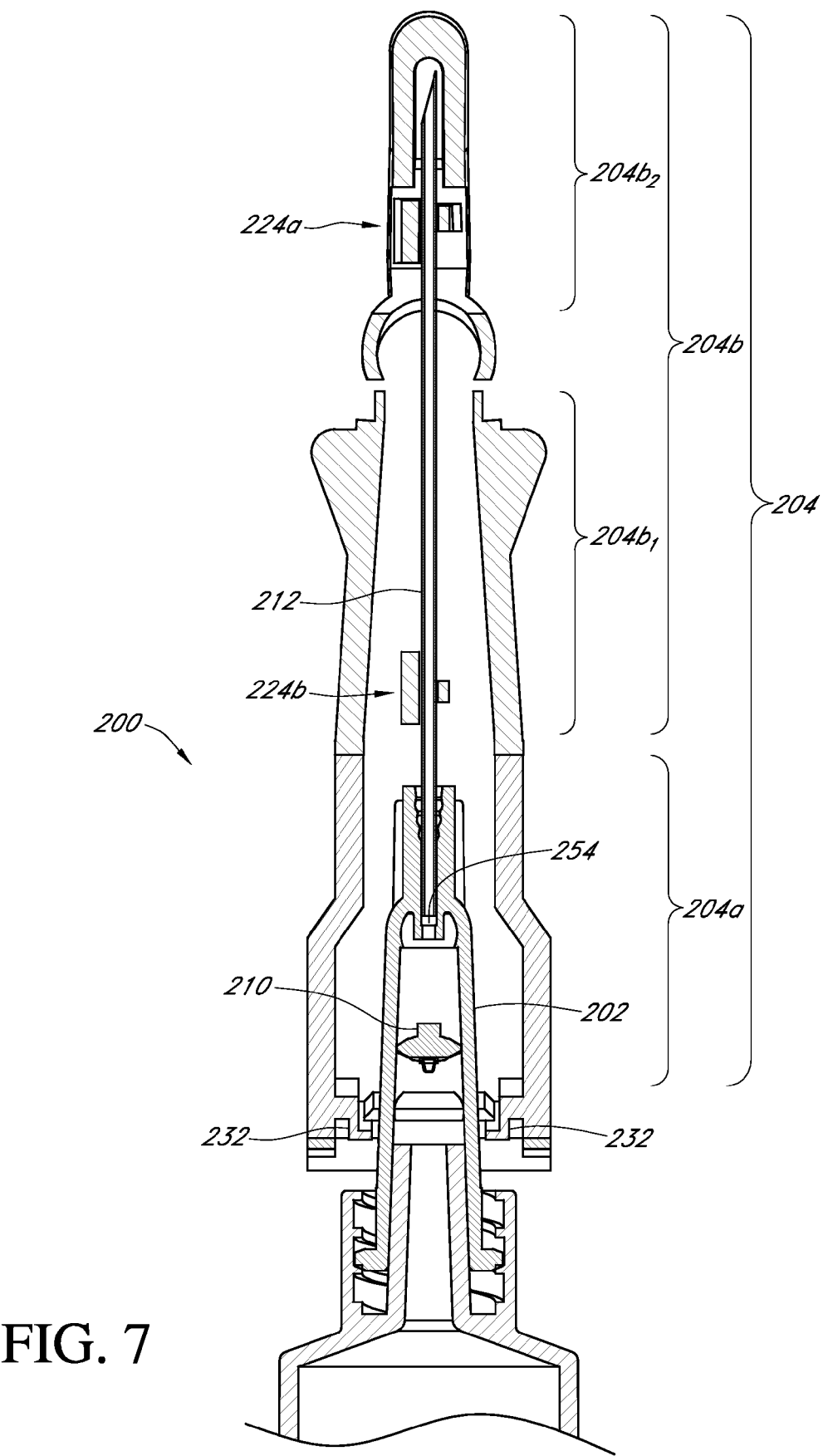
FIG. 7 illustrates a cross-sectional top view of an embodiment of a needleshield assembly in an extended position.

FIG. 7 illustrates a cross-sectional top view of the needleshield assembly 200 of FIGS. 2-3 in an extended position according to an embodiment of the present application. Some of the major components of the needleshield assembly 200 are shown in more detail in FIG. 7, including the dispensing device attachment member 202, the extensible frame 204 (including the proximal member 204a and the distal member 204b, and sub-portions 204b$_1$ and 204b$_2$) and the actuator 210. The needle 212 is also shown and may be an integral part of the needleshield assembly 200. In one embodiment, the needle 212 may be of a pre-cut length from approximately 0.5 inches (12.7 millimeters) to approximately 5.0 inches (127 millimeters), preferably 1.5 inches (38.1 millimeters), and may be of a standard material, such as stainless steel or plastic. The needle 212 may be seated within a counterbore 254 of the needleshield assembly 200 and glued into place; however, other means of attachment of the needle 212 within the counterbore 254 may be utilized. In some embodiments, the counterbore in which the needle 212 is situated may be at a depth to ensure constant needle height. FIG. 7 also shows first and second set of hooks 224a and 224b in representative positions on the needleshield assembly 200, which may function to render the needle 212 immovable once the extensible frame 204 is in the extended position. In some embodiments, hooks 224a and 224b may be an integral part of the needleshield assembly 200. FIG. 7 also shows hooking mechanism 232 which provides the additional safety features as explained previously. Embodiments of the present application may include one or more sets of hooks depending on the length of the needle to be rendered immovable.

In some embodiments, when in the extended position, needleshield assembly 100 may be from approximately 45.8 mm to 93.4 mm in length for needle lengths between 0.625 inches (15.875 mm) to 2.5 inches (63.5 mm). The length of the needleshield assembly 200 may be sized according to the size of the needle intended to be shielded. Needleshield assembly 200 may be manufactured from various materials, including, but not limited to, acrylonitrile butadiene styrene, polycarbonate, polyethylene, polypropylene, polyurethane and glass. Generally, the material should be of a type amenable for molding during the manufacturing process and safe for human contact.

Figure 8:
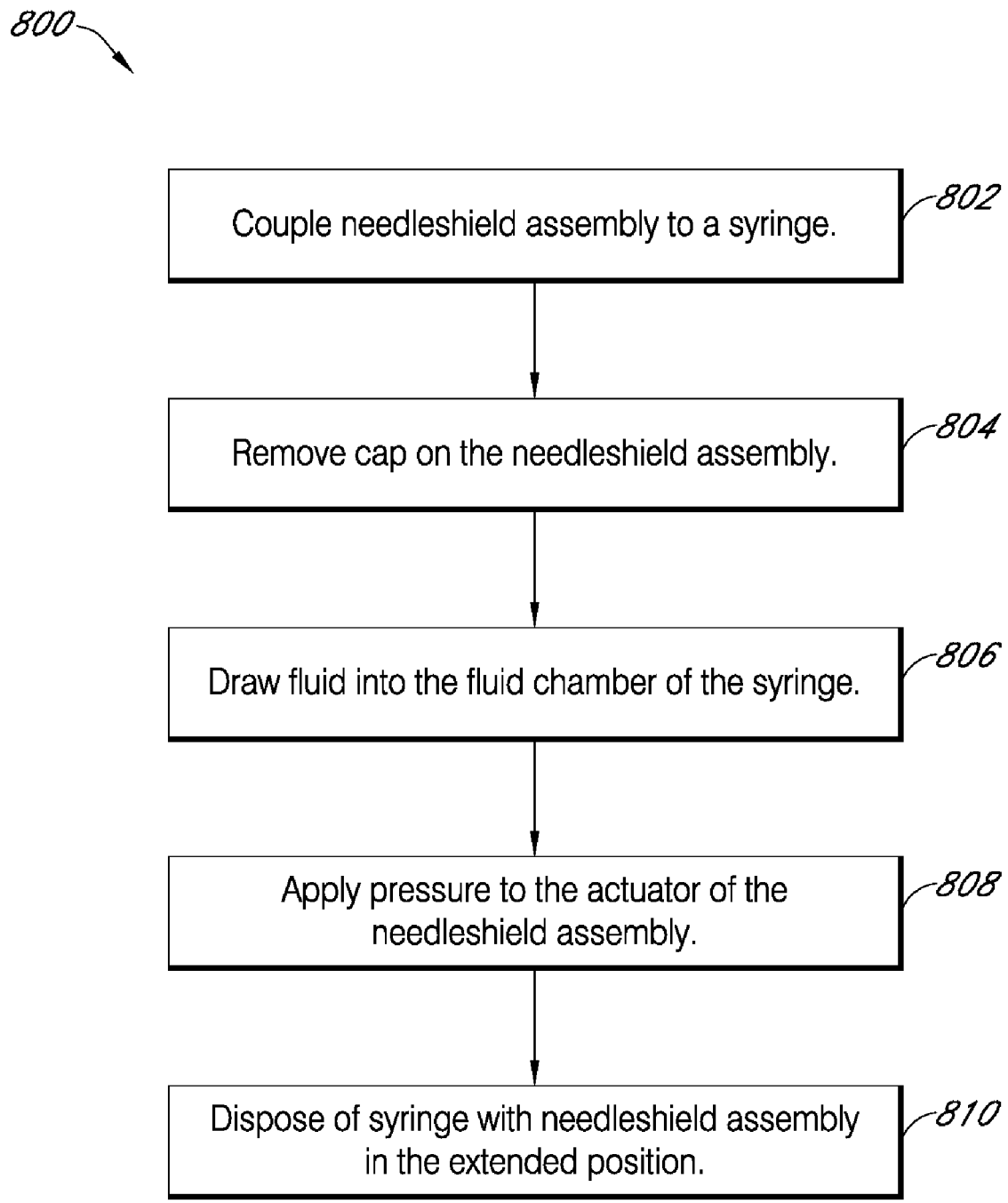
FIG. 8 illustrates an embodiment of a method of using a needleshield assembly.

FIG. 8 illustrates a method for using a needleshield assembly 800 according to an embodiment of the present application. In one embodiment, the needleshield assembly is coupled to a dispensing device by way of a dispensing device attachment member 802. A representative needleshield assembly may be, for example, similar to or the same as the needleshield assemblies described with reference to FIGS. 2-7. In this embodiment, the dispensing device is a syringe (without a needle). A removable cap protecting the needle on the needleshield assembly can then be removed 804. Thereafter, a user/operator may use the syringe in a customary manner, e.g., to draw fluid into the fluid chamber of the syringe 806. The fluid may be, but is not limited to, medication in liquid form or blood. If the fluid is medication, it may then be injected into a patient, an animal, an intravenous line or the like. Alternatively, if the fluid is blood, it may then be transferred to a lab tube for testing thereof. In other embodiments, the fluid chamber of the syringe may be configured to detach from the syringe body and function as a lab tube thereby eliminating the need to transfer the blood sample to a different lab tube. After use, the operator may apply pressure to the actuator of the needleshield assembly to effectuate a shielding function of the needleshield assembly 808. The shielding function may function in the manner described previously. Once in the extended position, the syringe with the needleshield assembly may be properly disposed 810.

Advantageously, the needleshield assembly according to embodiments of the present application may provide numerous mechanisms to prevent a needle from being used again after activating the actuator in the manner described previously. First, upon activation of the actuator, the portion of the sidewall that is lodged within the dispensing device attachment member may function to block the fluid path between the fluid chamber and the needle. Also, upon activation of the actuator, the blocking protrusion on the actuator additionally may block the fluid path and may be retained by the retaining member within the dispensing device attachment member. Moreover, the hooks may function to secure the needle and keep it immobile once the extensible frame is in the extended position. As a result, these mechanisms may either singly or combined function to prevent re-use of the needle after use thereof. Additionally, for manufacturing purposes, the needleshield assembly may be manufactured as one solid body sub-divided into several portions by hinges thereby realizing cost savings.

While certain exemplary embodiments have been described and shown in the accompanying drawings, it is to be understood that such embodiments are merely illustrative of and not restrictive on the broad application, and that this application is not limited to the specific constructions and arrangements shown and described, since various other modifications may occur to those ordinarily skilled in the art.

What is claimed is:

1. A needleshield assembly, comprising:
    a dispensing device attachment member adapted to attach the needleshield assembly to a needle hub of a dispensing device;
    an extensible frame comprising a distal member and a proximal member, the extensible frame connected to a proximal end of the dispensing device attachment member by a first hinge, the distal member and the proximal member connected by a second hinge at a distal end of the proximal member and a proximal end of the distal member, the extensible frame having a collapsed position and an extended position; and
    an actuator attached to the proximal end of the dispensing device attachment member by a third hinge, the actuator adapted to direct the extensible frame from the collapsed position to the extended position, the actuator further comprising
        a blocking protrusion adapted to puncture a wall of the dispensing device attachment member and block the fluid path when the extensible frame is in the extended position; and
        a retaining member adapted to secure the blocking protrusion in the fluid path.

2. The needleshield assembly of claim 1 wherein the distal member further comprises:
    a proximal sub-portion and a distal sub-portion;
    at least one aperture adapted to receive a distal end of the needle, the at least one aperture connecting the proximal sub-portion to the distal sub-portion of the distal member;
    at least one set of hooks adapted to immovably secure the needle when the extensible frame is in the extended position; and
    an enclosing member adapted to enclose the distal end of the needle when in the extended position, the enclosing member comprising the distal end of the distal sub-portion.

3. The needleshield assembly of claim 2 wherein a first set of hooks is positioned on a top face of the distal sub-portion and a second set of hooks is positioned on a bottom face of the proximal sub-portion.

4. The needleshield assembly of claim 3 wherein each set of hooks comprises two opposing members.

5. The needleshield assembly of claim 1, further comprising:
a hooking mechanism comprising a set of clips on a proximal end of the dispensing device attachment member and a set of corresponding latching mechanisms on a proximal end of the extensible member; and
a needle positioned within a bore of the dispensing device attachment member, the needle in fluid communication with a fluid chamber of the dispensing device forming a fluid path when attached to the dispensing device with the extensible frame in the collapsed position.

6. The needleshield assembly of claim 1, further comprising:
a pressure pad on the proximal member of the extensible frame and capable of contact with the actuator.

7. The needleshield assembly of claim 6 wherein a portion of the wall of the dispensing device attachment member functions to block the fluid path when the extensible frame is moved from the collapsed position to the extended position.

8. The needleshield assembly of claim 5, further comprising:
a removable cap to enclose the needle when the extensible frame is in the collapsed position.

9. The needleshield assembly of claim 8, further comprising:
a plurality of ribs about the periphery of the dispensing device attachment member for securing the removable cap.

10. A needleshield assembly, comprising:
a dispensing device attachment member adapted to attach the needleshield assembly to a needle hub of a dispensing device;
an extensible frame comprising a distal member and a proximal member, the extensible frame connected to a proximal end of the dispensing device attachment member by a first hinge, the distal member and the proximal member connected by a second hinge at a distal end of the proximal member and a proximal end of the distal member, the extensible frame having a collapsed position and an extended position, the distal member comprising:
a proximal sub-portion and a distal sub-portion;
at least one aperture adapted to receive a distal end of a needle, the at least one aperture connecting the proximal sub-portion to the distal sub-portion of the distal member;
at least one set of hooks adapted to immovably secure the needle when the extensible frame is in the extended position; and
an enclosing member adapted to enclose the distal end of the needle when in the extended position, the enclosing member comprising the distal end of the distal sub-portion; and
an actuator attached to the proximal end of the dispensing device attachment member by a third hinge, the actuator adapted to direct the extensible frame from the collapsed position to the extended position, the actuator comprising a blocking protrusion adapted to puncture a wall of the dispensing device attachment member and block the fluid path when the extensible frame is in the extended position; and
a retaining member adapted to secure the blocking protrusion in the fluid path.

11. The needleshield assembly of claim 10, wherein a first set of hooks is positioned on a top face of the distal sub-portion and a second set of hooks is positioned on a bottom face of the proximal sub-portion.

12. The needleshield assembly of claim 11, wherein each set of hooks comprises two opposing members.

13. The needleshield assembly of claim 10, further comprising:
a hooking mechanism comprising a set of clips on a proximal end of the dispensing device attachment member and a set of corresponding latching mechanisms on a proximal end of the extensible member; and
the needle, positioned within a bore of the dispensing device attachment member, in fluid communication with a fluid chamber of the dispensing device forming a fluid path when attached to the dispensing device with the extensible frame in the collapsed position.

14. The needleshield assembly of claim 10, further comprising:
a pressure pad on the proximal member of the extensible frame and capable of contact with the actuator.

15. The needleshield assembly of claim 14, wherein a portion of the wall of the dispensing device attachment member functions to block the fluid path when the extensible frame is moved from the collapsed position to the extended position.

16. The needleshield assembly of claim 13, further comprising:
a removable cap to enclose the needle when the extensible frame is in the collapsed position.

17. The needleshield assembly of claim 16, further comprising:
a plurality of ribs about the periphery of the dispensing device attachment member for securing the removable cap.

18. A needleshield assembly, comprising:
a dispensing device attachment member adapted to attach the needleshield assembly to a needle hub of a dispensing device;
an extensible frame comprising a distal member and a proximal member, the extensible frame connected to a proximal end of the dispensing device attachment member by a first hinge, the distal member and the proximal member connected by a second hinge at a distal end of the proximal member and a proximal end of the distal member, the extensible frame having a collapsed position and an extended position;
an actuator attached to the proximal end of the dispensing device attachment member by a third hinge, the actuator adapted to direct the extensible frame from the collapsed position to the extended position, the actuator comprising a blocking protrusion adapted to puncture a wall of the dispensing device attachment member and block the fluid path when the extensible frame is in the extended position; and
a retaining member adapted to secure the blocking protrusion in the fluid path;
a hooking mechanism comprising a set of clips on a proximal end of the dispensing device attachment member and a set of corresponding latching mechanisms on a proximal end of the extensible member; and
a needle, positioned within a bore of the dispensing device attachment member, in fluid communication with a fluid chamber of the dispensing device forming a fluid path when attached to the dispensing device with the extensible frame in the collapsed position.

* * * * *